United States Patent [19]

Baur et al.

[11] Patent Number: 5,004,837

[45] Date of Patent: Apr. 2, 1991

[54] PROCESS FOR PREPARING A CYCLOALKANONE AND/OR CYCLOALKANOL

[75] Inventors: Henricus A. C. Baur, Herten; Ubaldus F. Kragten, Beek, both of Netherlands

[73] Assignee: Stamicarbon B.V., Geleen, Netherlands

[21] Appl. No.: 424,706

[22] Filed: Oct. 20, 1989

[30] Foreign Application Priority Data

Oct. 21, 1988 [NL] Netherlands .......................... 8802592

[51] Int. Cl.$^5$ ............................................. C07D 45/53
[52] U.S. Cl. ..................................... 568/342; 568/835
[58] Field of Search ................. 568/342, 385, 835, 836

[56] References Cited

U.S. PATENT DOCUMENTS

| | | |
|---|---|---|
| 4,459,427 | 7/1984 | Middleton et al. .................. 568/342 |
| 4,482,746 | 11/1984 | Hermolin ............................ 568/342 |
| 4,499,305 | 2/1985 | Hermolin ............................ 568/342 |
| 4,659,829 | 4/1987 | Saussine et al. ..................... 568/385 |

FOREIGN PATENT DOCUMENTS

| | | | |
|---|---|---|---|
| 0027937 | 5/1981 | European Pat. Off. ............ | 568/342 |
| 270468 | 6/1988 | European Pat. Off. ............ | 568/342 |
| 3222143 | 12/1983 | Fed. Rep. of Germany ...... | 568/342 |
| 60-126237 | 7/1985 | Japan ................................. | 568/342 |

OTHER PUBLICATIONS

"Mono-Oxygenase-Like Oxidation of Hydrocarbons Using Supported Manganese-Porphyrin Catalysts: Beneficial Effects of a Silica Support for Alkane Hydroxylation", J. Chem. Soc., Commun., 1989, pp. 1149-1151.

Primary Examiner—James H. Reamer
Attorney, Agent, or Firm—Cushman, Darby & Cushman

[57] ABSTRACT

The invention relates to a process for preparing a cycloalkanone and/or cycloalkanol by oxidation of a cycloalkane using oxygen to form a hydroperoxide, followed by a decomposition of the hydroperoxide, in the presence of an organic metal complex, the decomposition being carried out in the presence of a phthalocyanine or porphyrin metal complex immobilized on a carrier material.

8 Claims, No Drawings

PROCESS FOR PREPARING A CYCLOALKANONE AND/OR CYCLOALKANOL

The invention relates to a process for preparing a cycloalkanone and/or cycloalkanol by oxidation of a cycloalkane with 5-12 carbon atoms using oxygen to form a cycloalkylhydro-peroxide, followed by a decomposition of the cycloalkylhydro-peroxide in the presence of an organic metal complex.

Such a process is described in JP-A-60.126.237. As a result of such a process, a mixture of a cycloalkanone (or ketone, K) and a cycloalkanol (or alcohol, A) is obtained, which mixture, based on the reaction products, is sometimes described also as K/A mixture.

In literature, attention is frequently given to the oxidation of cycloalkanes, particularly cyclohexane. Here a distinction can be made between two process steps: first of all the conversion of the cycloalkane to form a mixture substantially containing the corresponding cycloalkylhydroperoxide, followed by a conversion (decomposition) of this cycloalkylhydroperoxide to form the K/A mixture. In this second step, besides the direct conversion of the cycloalkylhydroperoxide, a reaction often takes place also of the cycloalkylhydroperoxide with the cycloalkane still present to a high degree, which again results in the formation of K and A. In a number of cases this so-called cycloalkane participation plays an essential part in the total conversion of the cycloalkane and the yield of the K/A mixture that goes with it.

All sorts of catalyst systems have been proposed for carrying out the said process. They relate to carrying out either the first step, the oxidation, or the second step, the decomposition, or both. For instance, in FR-A-1.530.986 the preparation of a hydroperoxide is described, in which, besides a complexing agent, a transition metal complex may be present. In EP-A-0.027.937 a transition metal complex of certain iso-indolines is used in the conversion of cyclohexane to a K/A mixture. EP-A-0.270.468 describes the use of a soluble ruthenium compound in combination with certain iso-indoline compounds in the decomposition step.

JP-A-60.126.237 describes the use of an organometallic complex with the metal bonded to a porphyrin structure, the metal used being Co, Mn, Cr or Fe.

All the processes mentioned use the metal complex in a soluble form, i.e. the complex is present in the oxidation liquid in a homogeneously dissolved state. As a result, the K/A mixture must necessarily be separated from the complex separately, for instance by distillation. Besides the fact that, owing to such thermal action, (a part of) the thermally sensitive complex is lost, it is necessary for the complex to be recovered from the distillation product before it can be used in the process again. In a number of cases the selectivity of the conversion to K and A, too, is not quite satisfactory.

There is, therefore, a need for a process in which the above and other disadvantages of the known processes are overcome. This is achieved according to the invention in that in the preparation of the cycloalkanol and/or cycloalkanone the decomposition of the cycloalkylhydroperoxide is carried out in the presence of a phthalocyanine or porphyrin complex immobilized on a carrier material. Owing to the immobilization on the carrier material, a catalyst is obtained that can easily be separated from the reaction phase and which combines a surprisingly and yet unexplainable good, sustained and stable activity with a good selectivity in respect of the ketone and/or alcohol, compared to a process in which a homogeneously dissolved complex is used, as is done in aforementioned JP-A-60.126.237.

Phthalocyanine and porphyrin complexes applicable in a process according to the invention are known per se. In this connection reference can be made to, for instance, the article by J. Manassen in Cat. Rev. Sci. Eng. 9(2), 223 -43 (1974), as well as, in so far as porphyrin complexes are concerned, to the above-mentioned JP-A-60.126.237. As starting material for the said complexes a porphyrin or a phthalocyanine is proceeded from, which may be substituted. The structural formulas of these compounds are as follows:

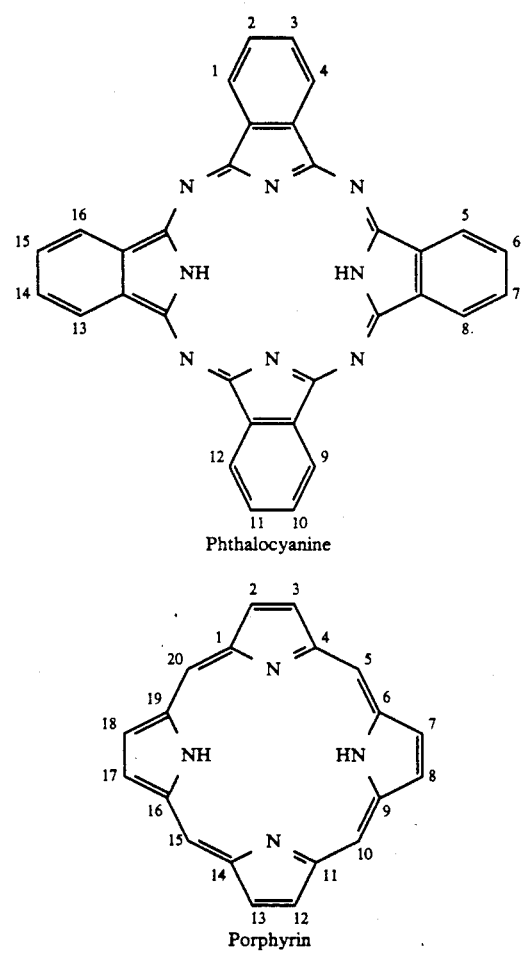

Phthalocyanine

Porphyrin

Phthalocyanines may be substituted at the indicated positions 1-16, porphyrins at the indicated positions 1-20, except for positions 1, 4, 6, 9, 11, 14, 16 and 19. The substituents applied may be:

a. H, F, Cl, Br, I,
b. alkyl groups, whether or not substituted,
c. alkenyl groups, whether or not substituted,
d. phenyl groups, whether or not substituted,
e. amines, sulphonic acids, carboxylic acids, aldehydes and derivatives thereof.

The metalation of a porphyrin can be effected by introducing porphyrin into dimethylformamide (DMF) and adding the metal to be incorporated as metal chloride under reflux. Phthalocyanines can be synthesized by proceeding from molecular fragments, such as phthalonitrile, phthalimide and phthalic anhydride. As metal source, metal chlorides can be used. In some cases urea is used as nitrogen donor and ammonium molybdate as catalyst.

As metals most suited for applying the process can be mentioned: Co, Mn, Cr, Fe and/or V, but in principle any transition metal will qualify that is capable of forming organometallic complexes with said products. Mixtures of the said metals can be applied also.

According to the invention the organometallic complexes are bonded to (immobilized on) a carrier material. The carrier material applied may be any material with which a bond with the complex can be achieved. In this connection an ionic bond as well as a covalent bond is applicable. In order to achieve an effective bond, the substituted groups of the organometallic complexes must be such as to make such covalent or ionic bond possible. This can be achieved, for instance, by using complexes containing one or more sulphonic acid, amino acid or carboxylic acid groups, or combinations thereof.

The level of loading of the organometallic complex is dependent upon the following parameters: type of complex (i.e., phthalocyanine or porphyrin); type of metal; and type of carrier. The degree of loading can be expected to range from 0.01 to 5.0 wt. %, relative to the complex plus carrier.

The carrier material to be used may be of an inorganic as well as an organic polymeric nature. The carrier material, too, must be provided with one or more groups that can bring about the immobilization of the organometallic complex. One of the requirements imposed in respect of the carrier material is that the carrier material must have enough reactive groups in order thus to obtain an acceptable degree of loading. The suitable reactive groups can be, for instance, COOH, NHR, OH, SO$_3$H, Cl, Br, I, but also phenyl and related groups. Further, the material must not dissolve in one of the components present in the process flow, it must be inert to the reactions which occur and it must have sufficient mechanical stability.

As carrier, inorganic carriers, such as alumina, TiO$_2$, SiO$_2$ or organic carriers, such as modified polystyrene, EVA copolymer, acid- or anhydride-modified PE, are suitable.

When using, for instance, silica as carrier material, the bonding can be effected, for instance, by starting from a phthalocyanine or porphyrin with one or more halogen (compounds)-containing substituents. The starting material can be heated for some time in pyridine together with the silica. The solid is subsequently filtered off, washed and dried.

When using, for instance, polystyrene as carrier material the bonding can be effected, for instance, by starting from a phthalocyanine or porphyrin with one or more substituents containing COOH groups. By means of a Friedel-Crafts reaction this can be bonded to polystyrene.

In the process according to the invention the oxidation of the cycloalkane is carried out as known in the art in the liquid phase at temperatures of 120–200° C., particularly 140–180° C., using, for instance, air, pure oxygen or a mixture of oxygen and inert gas. In the process an amount of, for instance, 1–12% of the cycloalkane is converted. The pressure is not critical in this oxidation process and is mostly between 4 and 50 bar.

Preference is given to carrying out the oxidation of the cycloalkane in the absence of materials promoting the decomposition of the cycloalkylhydroperoxide formed, such as compounds of transition metals, and that is why for this oxidation process preference is given to the use of a reactor with an inert inner wall, for instance an inner wall of passivated steel, aluminium, glass, enamel and similar materials. If yet the application of an oxidation catalyst is desired, the amount of transition metal should preferably be very small, for instance in the order of 1–10 parts by weight per million. The oxidation catalyst used may be a compound of, for instance, cobalt, chromium, manganese, iron, nickel, copper or mixtures thereof. The immobilized organometallic complexes described in this application are suitable also.

The decomposition of the cycloalkylhydroperoxide in the oxidation mixture is effected by means of the immobilized metal complexes based on phthalocyanine or porphyrin. The decomposition catalyst can be applied in various ways. As it is immobilized on a carrier, slurry reactors as well as, for instance, packed beds can be used for realizing the conversion of the cycloalkylhydro-peroxide. The heat of reaction released in the decomposition must be collected and carried off adequately in order to guarantee a proper process temperature control. This can be well done in particular when using slurry reactors. During the decomposition the desired temperature can then, for instance, be maintained by reflux cooling, preferably during a reactifying treatment, for at least a part of the heat to be carried off. This has a certain favourable effect on the yield of the desired product. The amount of immobilized complex to be used is under such conditions for instance 5–250 ppm metal calculated on the oxidation mixture. Preference is given to the use of 10–150 ppm metal.

During the decomposition the temperature is generally within the range of 25–120° C. In the decomposition the chosen pressure is usally somewhat lower than in the oxidation. The decomposition is preferably carried out in the presence of oxygen. The yield of K/A mixture is thus improved.

Before the decomposition of the hydroperoxide in the oxidation mixture, the oxidation mixture can be treated, if so desired, with water or with an aqueous alkalihydroxide or alkalicarbonate solution for the purpose of removing and/or neutralizing the acids formed in the oxidation, for instance to a pH of the aqueous phase of 8–13. In addition, the oxidation mixture can be preconcentrated, for instance by a distillation or a flashing step.

The reaction mixture obtained as a result of the decomposition of the hydroperoxide can be further processed by subjecting the organic phase, after washing with water if so desired, to a distillation process while recovering cycloalkane for recycling, as well as cycloalkanol and cycloalkanone. The process is particularly suited for the oxidation of cyclohexane, the reaction products of which can particularly be used either for the preparation of caprolactam (for nylon 6) or for the preparation of adipic acid (for nylon 6,6). The cyclohexanol and cyclohexanone thus obtained have been found without further processing to be pure enough for further conversion into caprolactam.

The invention will be further elucidated by means of the following examples.

EXAMPLE I

To 35 ml DMF, 5 mmoles dicyclohexylcarbodiimide was added at room temperature. Subsequently, 0.5 mmole Co-tetrasulphonic acid phthalocyanine was added. This mixture was stirred for one hour at room temperature. Subsequently, 1 gramme of a silica containing amine groups was added (Polygosil-NH$_3$). This mixture was stirred at room temperature for 12 hours, filtered and washed with ethanol and dichloromethane and dried at 60C. The resulting product was analyzed for, among other things, its metal content (0.39 wt. % relative to complex plus carrier).

EXAMPLE II

Example I was repeated, the compound to be bonded being the Cu-tetrasulphonic acid phthalocyanine.

EXAMPLE III

Example I was repeated, the compound to be bonded being the Mn-tetrasulphonic acid phthalocyanine.

EXAMPLE IV

To a solution of cobalt tetrabromophthalocyanine in pyridine, 10 grammes silica (balls with a diameter of 3 mm and a BET surface of about 60 m$^2$/gram) was added. The suspension was stirred for 6 hours at 70° C. After cooling, the suspension was filtered and washed with methanol and chloroform and dried. The reaction product was analyzed for its metal content (0.05 wt. %).

EXAMPLE V

Example IV was repeated, the compound to be bonded being Comonochlorophthalocyanine (containing 0.08 wt. % Co).

EXAMPLE VI

Example IV was repeated, the compound to be bonded being 5(4(3-bromo-1-propoxy)phenyl), 10,15,20-tritolylporphyrin. After bonding, Cr, Co, V, Mn and Fe were incorporated as metals, using the DMF method. All these products were analyzed for their metal content.

| Results: | Cr: 0.09 wt. % | Mn: 0.06 wt. % |
|---|---|---|
| | Co: 0.05 wt. % | Fe: 0.06 wt. % |
| | | V: 0.04 wt. % |

EXAMPLE VII

To a cyclohexane oxidation mixture containing, per kilogramme, 200 mmoles cyclohexylhydroperoxide (CHHP), 60 mmoles cyclohexanol and 30 mmoles cyclohexanone, such an amount of the silica-bonded Co-phthalocyanine from example I was added at 80° C. that the final metal concentration in the mixture was 70 ppm. The mixture was stirred until all CHHP was found, on the grounds of a titrimetric peroxide analysis, to be broken off. The velocity constant k (based on a first order reaction) was 0,15 min-1. The selectivity in respect of K+A was 97.5% with a K/A ratio of 0.67. The turnover number in reuse (being the number of moles of converted product per mole metal in the complex) was higher than 50,000.

EXAMPLE VIII

Example VII was repeated with the same catalyst, but now also air was passed through during the decomposition. The selectivity in respect of K+A was 114% with a K/A ratio of 0.59. The turnover number in re-use was higher than 50,000.

COMPARATIVE EXPERIMENT A

Example VIII was repeated with Co-phthalocyanine as catalyst. The catalyst did not dissolve completely in the reaction mixture (suspension) and could be recovered again partially by filtration. The k was 0.012 min-1. The selectivity in respect of K+A was 112% at a K/A ratio of 0.56. The turnover number in re-use was about 500.

COMPARATIVE EXPERIMENT B

Example VII was repeated with the homogeneously dissolved Co-2-ethylhexanoate as catalyst. The k was 0.02 min-1 calculated on the first 20 minutes of the decomposition. After these 20 minutes the catalyst activity decreased very strongly. The selectivity in respect of K+A was 91.6% with a K/A ratio of 0.45. Re-use of the catalyst was not possible. Comparing examples VII and VIII with experiments A and B, it can be seen, that the presence of a carrier material is essential in order to obtain:

(a) an increased activity towards K+A
(b) a long and stable activity of the catalyst
(c) a good selectivity of the process.

Further, there is notably the very distinct and positive influence of the presence of oxygen during the decomposition.

EXAMPLE IX

To 20 ml thionyl chloride, 4 mmoles Co-tetracarboxyphthalocyanine was added. This mixture was stirred for a few hours at room temperature in an N2 atmosphere. Subsequently, a suspension of 1,1,2,2-tetrachloroethane and polystyrene (20 grammes, 3% vinyl benzene, 22-50 mesh, macroporous 8000 nm) was added. The reaction mixture was heated to 135° C. and the excess of SOCl$_2$ was distilled off. The reactor mass was cooled down to 12° C., upon which 6 grammes AlCl$_3$ was added to it. The reaction mixture was stirred for 20 hours. Subsequently, the solid material was filtered, washed with 1,1,2,2-tetrachloroethane, methanol, basic water and 1 N HCL. The resulting solid material was dried at 50° C. The product was analyzed for its metal content (0.43 wt. %).

EXAMPLE X

Example IX was repeated, the compound to be bonded being Mn-octacarboxyphthalocyanine (0.53 wt. %).

EXAMPLE XI

Example IX was repeated, the compound to be bonded being the 5,10,15,20-tetra(4-carboxyphenyl)porphyrin. After bonding, Cr, Co, Mn, Cu and Fe were incorporated as metals, using the DMF method. All the products were analyzed for their metal content.

| Results: | Cr = 1.9 wt. % | Mn = 0.61 wt. % |
|---|---|---|
| | Co = 0.49 wt. % | Cu = 0.50 wt. % |
| | | Fe = 0.64 wt. % |

EXAMPLE XII

Example VII was repeated, the catalyst being the polystyrene-bonded Cr-porphyrin of example XI. The catalyst could be re-used a plurality of times. The k was 0.028 min-1. The selectivity in respect of K+A was 96.0% with a K/A ratio of 4.2.

EXAMPLE XIII

Example VII was repeated, the catalyst being the polystyrene-bonded Fe-porphyrin of example XI. The catalyst could be re-used a plurality of times. The k was 0.19 min-1; the K/A ratio was 2.8.

EXAMPLE XIV

Example VII was repeated, the catalyst being the polystyrene-bonded Co-porphyrin of example XI. The catalyst could be re-used a plurality of times. The k was 0.18 min-1; the K/A ratio was 1.0.

COMPARATIVE EXPERIMENT C

Example VII was repeated, the catalyst being the homogeneously dissolved Cr-2-ethyl-hexanoate. The k was 0.008 min-1. The selectivity in respect of K+A was 91.7% with a K/A ratio of 4.4. The catalyst could not be used again.

We claim:

1. Process for preparing a cycloalkanone and/or cycloalkanol by oxidation of a cycloalkane with 5-12 carbon atoms using oxygen to form a cycloalkylhydroperoxide, followed by a decomposition of the cycloalkylhydroperoxide in the presence of an organic metal complex, characterized in that the decomposition of the cycloalkylhydroperoxide is carried out in the presence of a phthalocyanine or porphyrin metal complex immobilized on a carrier material.

2. Process according to claim 1, characterized in that the metal in the complex is Co, Mn, Cr, Fe and/or V.

3. Process according to claim 1, characterized in that the carrier material is of an inorganic nature.

4. Process according to claim 1, characterized in that the carrier material is of an organic polymeric nature.

5. Process according to claim 1, characterized in that the decomposition is carried out in a slurry reactor.

6. Process according to claim 5, characterized in that 10–150 ppm metal complex calculated on the metal in the complex and on the oxidation mixture is used.

7. Process according to claim 1, characterized in that the decomposition of the cycloalkylhydroperoxide is carried out in the presence of oxygen.

8. The process according to claim 1, wherein said phthalocyanine or porphyrin is substituted with substituents selected from the group consisting of H, F, Cl, Br, I, substituted alkyl groups, unsubstituted alkenyl groups, substituted alkenyl groups, unsubstituted alkenyl groups, substituted phenyl groups, unsubstituted phenyl groups, amines, sulphonic acids, carboxylic acids, aldehydes, and derivatives thereof.

* * * * *

UNITED STATES PATENT AND TRADEMARK OFFICE
CERTIFICATE OF CORRECTION

PATENT NO. : 5,004,837

DATED : April 2, 1991

INVENTOR(S) : Baur et al

It is certified that error appears in the above-indentified patent and that said Letters Patent is hereby corrected as shown below:

Claim 8, column 8, line 21, change "C1" to --Cl--;

column 8, line 22, change "alkenyl" to --alkyl--; and

Signed and Sealed this

Thirteenth Day of July, 1993

Attest:

MICHAEL K. KIRK

*Attesting Officer*    *Acting Commissioner of Patents and Trademarks*